US008685927B2

(12) United States Patent
Dal Farra et al.

(10) Patent No.: US 8,685,927 B2
(45) Date of Patent: *Apr. 1, 2014

(54) COSMETIC AND/OR PHARMACEUTICAL COMPOSITION COMPRISING A RELIEVING PEPTIDIC HYDROLYZATE

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 113 days.

This patent is subject to a terminal disclaimer.

(21) Appl. No.: 13/264,082

(22) PCT Filed: Apr. 15, 2010

(86) PCT No.: PCT/FR2010/000312
§ 371 (c)(1),
(2), (4) Date: Oct. 12, 2011

(87) PCT Pub. No.: WO2010/119192
PCT Pub. Date: Oct. 21, 2010

(65) Prior Publication Data
US 2012/0094921 A1 Apr. 19, 2012

(30) Foreign Application Priority Data
Apr. 15, 2009 (FR) ...................................... 09 01824

(51) Int. Cl.
A61K 38/07 (2006.01)
A61K 38/08 (2006.01)
A61K 8/64 (2006.01)
A61K 8/97 (2006.01)
C07K 5/10 (2006.01)
C07K 7/06 (2006.01)
C07K 4/10 (2006.01)
A61Q 17/00 (2006.01)
A61Q 17/04 (2006.01)

(52) U.S. Cl.
USPC ......... 514/18.6; 514/18.8; 530/329; 530/330; 530/331

(58) Field of Classification Search
CPC ..... A61K 38/07; A61K 38/08; A61K 38/011; A61K 8/64; A61K 8/97; C07K 5/10; C07K 7/06; C07K 5/1008; C07K 4/10; A61Q 17/00; A61Q 17/04; A61Q 19/004; A61Q 19/005
USPC ................. 514/18.6, 18.8; 530/329, 330, 331
See application file for complete search history.

(56) References Cited

U.S. PATENT DOCUMENTS

| 4,139,619 A | 2/1979 | Chidsey, III |
| 4,596,812 A | 6/1986 | Chidsey, III et al. |
| 5,733,558 A | 3/1998 | Breton et al. |
| 5,977,082 A | 11/1999 | Gatti et al. |
| 7,431,919 B2 | 10/2008 | Travkina et al. |
| 7,887,858 B2 | 2/2011 | Cauchard et al. |
| 8,394,390 B2 | 3/2013 | Galeotti et al. |
| 2004/0141939 A1 | 7/2004 | Dal Farra et al. |
| 2005/0272097 A1 | 12/2005 | Calenoff |
| 2007/0274937 A1 | 11/2007 | Dal Farra et al. |
| 2008/0268077 A1 | 10/2008 | Vielhaber |

FOREIGN PATENT DOCUMENTS

| EP | 0265099 | 4/1988 |
| EP | 0327263 | 8/1989 |
| EP | 0695801 | 2/1996 |
| EP | 0738510 | 10/1996 |
| EP | 0902035 | 3/1999 |
| EP | 1152062 | 11/2001 |
| EP | 1281401 | 2/2003 |
| EP | 1272148 | 6/2006 |
| EP | 1707189 | 10/2006 |
| FR | 2789312 | 8/2000 |
| FR | 2868309 | 10/2005 |
| FR | 2887772 | 1/2007 |
| FR | 2904552 | 2/2008 |
| FR | 2911779 | 8/2008 |
| FR | 2915384 | 10/2008 |
| FR | 2925325 | 6/2009 |
| FR | 2925326 | 6/2009 |
| FR | 2925327 | 6/2009 |
| FR | 2925330 | 6/2009 |
| FR | 2927254 | 8/2009 |
| JP | 07-316023 | 12/1995 |
| WO | 03/008438 | 1/2003 |
| WO | 03/023067 | 3/2003 |
| WO | 03/068184 | 8/2003 |
| WO | 03/087831 | 10/2003 |
| WO | 2004/031211 | 4/2004 |
| WO | 2004/058282 | 7/2004 |
| WO | 2004/096168 | 11/2004 |
| WO | 2005/047328 | 5/2005 |
| WO | 2005/080985 | 9/2005 |
| WO | 2005/107697 | 11/2005 |
| WO | 2005/111081 | 11/2005 |
| WO | 2008/015343 | 2/2008 |

OTHER PUBLICATIONS

Dal Farra et al, machine translation of FR 2915384, pp. 1-18. Apr. 27, 2007.*
Dal Farra et al, machine translation of FR 2904552, pp. 1-16. Aug. 3, 2006.*
Effects of Aging on the Skin, from Merck manual, p. 1. Accessed Apr. 9, 2012.*
Chronic effects of Sunlight from Merck manual, pp. 1-2. Accessed Aug. 23, 2012.*

(Continued)

Primary Examiner — Julie Ha
(74) Attorney, Agent, or Firm — Thompson Hine L.L.P.

(57) ABSTRACT

A cosmetic or pharmaceutical composition that includes a peptide hydrolyzate which is enriched in soothing bioactive peptide in a physiologically acceptable medium is described. Methods for applying such compositions to the skin are also described, in particular where the active principle activates 3-hydroxy-3-methylglutaryl-Coenzyme A (HMG-CoA) reductase in skin cells to treat skin irritations.

15 Claims, 2 Drawing Sheets

(56) References Cited

OTHER PUBLICATIONS

Alopecia from Merck manual, pp. 1-5. Accessed Jul. 2, 2013.*
PCT, International Search Report, International Application No. PCT/FR2010/000312 (mailed Jul. 22, 2010; published Oct. 21, 2010).
Luskey, K.L. et al., "Human 3-Hydroxy-3-methylglutaryl Coenzyme A Reductase," *The Journal of Biological Chemistry*, vol. 260, No. 18, p. 10271-10277 (Aug. 25, 1985).
Menon, G.K. et al., "De novo sterologenesis in the skin. II. Regulation by cutaneous barrier requirements," *Journal of Lipid Research*, vol. 26, pp. 418-427 (1985).
Proksch, E. et al., "Barrier function regulates epidermal lipid and DNA synthesis," *British Journal of Dermatology*, 128, pp. 473-482 (1993).
"Designing Custom Peptides," from SIGMA Genosys, http://www.sigma-genosys.com/peptide_design.asp, pp. 1-2, (accessed Dec. 16, 2004).
Berendsen, H.J.C., "A Glimpse of the Holy Grail?" Science, 1998, 282: 642-643.
Bradley, C.M. et al., "Limits of Cooperativity in a Structurally Modular Protein: Response of the Notch Ankyrin Domain to Analogous Alanine Substitutions in Each Repeat," J. Mol. Biol., 2002, 324: 373-386.
Definition of "derivative" from http://cancerweb.ncl.ac.uk/omd/about.html, pp. 1-5 (accessed Jul. 7, 2005).
Ngo, J.T. et al., "Computational Complexity Protein Structure Prediction, and the Levinthal Paradox, The Protein Folding Problem and Tertiary Structure Prediction," K. Merc Jr. and S. Le Grand Edition, 1994, pp. 491-495.
Rudinger, J., "Characteristics of the amino acids as components of a peptide hormone sequence," Peptide Hormones, J.A. Parsons Edition, University Party Press, Jun. 1976, pp. 1-7.
Schinzel, R. et al., "The phosphate recognition site of *Escherichia coli* maltodextrin phosphorylase," FEBS, Jul. 1991, 286(1,2): 125-128.
Voet, D. et al., Biochemistry, Second Edition, John Wiley & Sons, Inc., 1995, pp. 235-241.
PCT, International Preliminary Report on Patentability, International Application No. PCT/FR2010/000312 (Nov. 1, 2011).
Ghadially, R. et al., "The Aged Epidermal Permeability Barrier," The Journal of Clinical Investigations, Inc., vol. 95, pp. 2281-2290 (May 1995).
Gourley, D.G., et al., "HMG—CoA Reductase: a Novel Target for Antimicrobial Chemotherapy," Abstracts of the Interscience Conference on Antimicrobial Agents and Chemotherapy, vol. 43, 2003, p. 219, XP035587 & 43rd Annual Interscience Conference on Antimicrobial Agents and Chemotherapy, Chicago, IL, USA, Sep. 14-17, 2003 (abstract).
Kullmann, W., "Proteases as Catalysts for Enzymic Syntheses of Opioid Peptides," The Journal of Biological Chemistry, vol. 255, No. 17, pp. 8234-8238 (Sep. 10, 1980).
Martini, M.C., "Biochemical Analysis of epidermal lipids," Pathologie Biologie, 51, pp. 267-270 (2003).
Norlén, L. et al., "Inter- and Intra-Individual Differences in Human Stratum Corneum Lipid Content Related to Physical Parameters of Skin Barrier Function In Vivo," J. Invest. Dermatol., 112 (1), pp. 72-77 (1999).
Birch, M.P. et al., "Hair density, hair diameter and the prevalence of female pattern hair loss," British Journal of Dermatology, 144, pp. 297-304 (2001).
Courtois, M. et al., "Ageing and hair cycles," British Journal of Dermatology, 132, pp. 86-93 (1995).
Langbein, L. et al., "The Catalog of Human Hair Keratins," The Journal of Biological Chemistry, vol. 276, No. 37, pp. 35123-35132 (Sep. 14, 2001).
Lenoir, M.-C. et al., "Outer Root Sheath Cells of Human Hair Follicle Are Able to Regenerate a Fully Differentiated Epidermis in Vitro," Developmental Biology, vol. 130, pp. 610-620 (1988).
Pelfini, C. et al., "Cheveux et vieillissement," J. Méd. Esth. et Chir. Derm., vol. XIV, No. 53, pp. 9-14 (Mar. 1987).
Porter, R.M. et al., "Keratin K6irs is specific to the inner root sheath of hair follicles in mice and humans," British Journal of Dermatology, 145, pp. 558-568 (2001).
SEQ ID No: 30601 from U.S. Appl. No. 8,394,390 (Mar. 2013).

* cited by examiner

Figure 1 HPLC chromatogram of a einkorn hydrolyzate
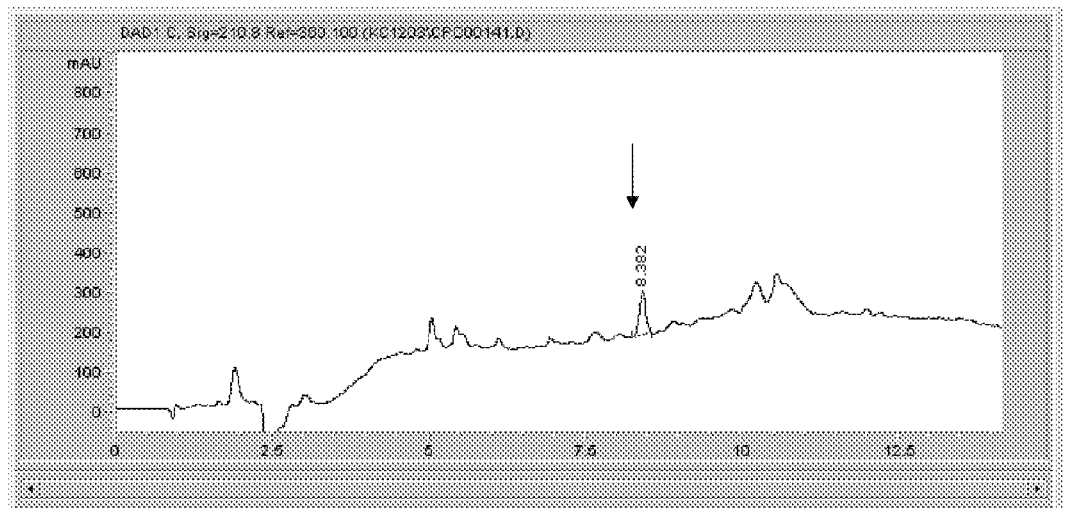
Figure 2 HPLC chromatogram of a potato hydrolyzate
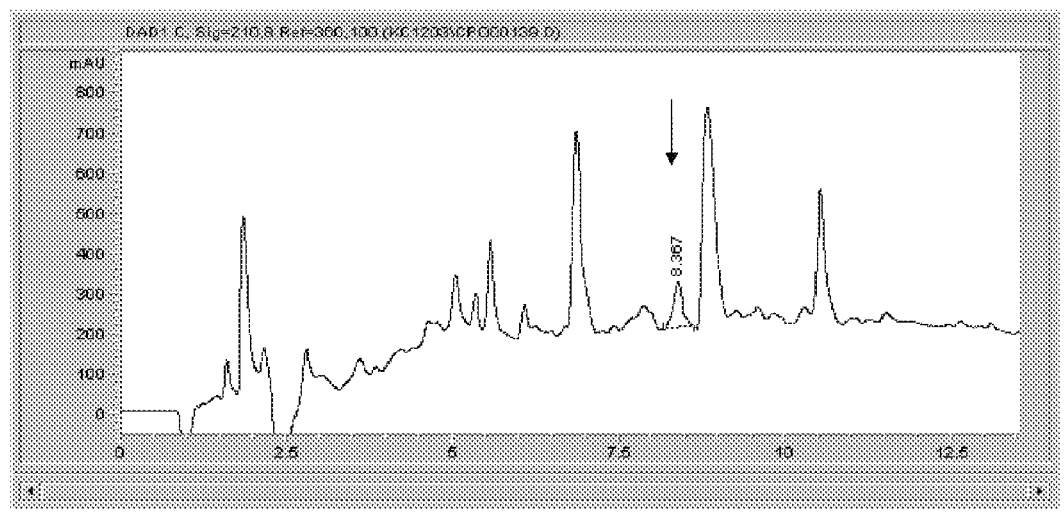

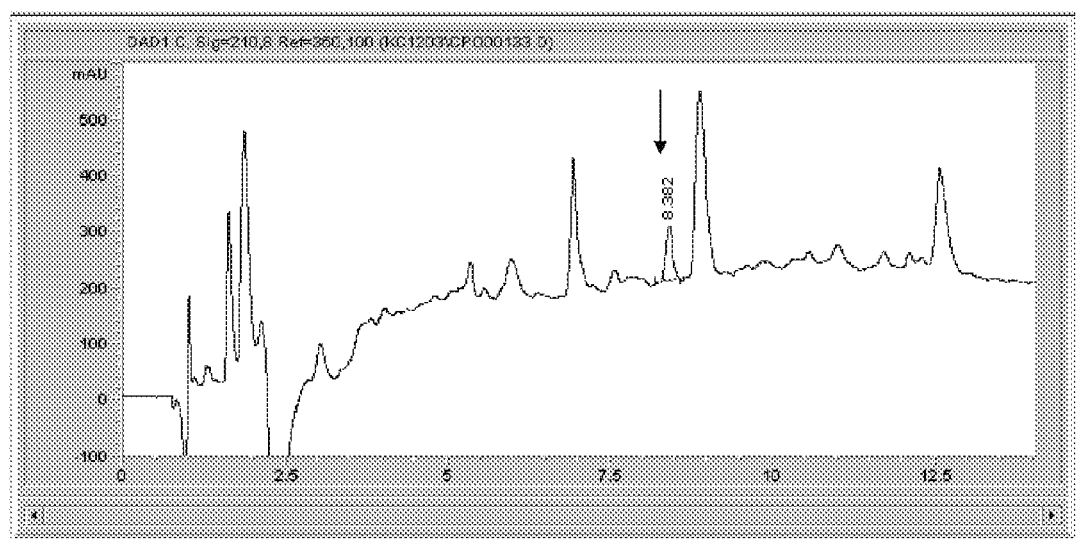
Figure 3 HPLC chromatogram of a corn hydrolyzate

SEQUENCE LISTING

```
<160> NUMBER OF SEQ ID NOS: 7

<210> SEQ ID NO 1
<211> LENGTH: 6
<212> TYPE: PRT
<213> ORGANISM: Triticum monococcum
<220> FEATURE:
<221> NAME/KEY: MISC_FEATURE
<223> OTHER INFORMATION: The sequence also may be obtained from Solanum
      tuberosum, Zeamayz L, Hordeum vulgare, or Brassica napus.

<400> SEQUENCE: 1

Ala Glu Gly Leu Ser Ile
1               5

<210> SEQ ID NO 2
<211> LENGTH: 5
<212> TYPE: PRT
<213> ORGANISM: Triticum monococcum
<220> FEATURE:
<221> NAME/KEY: MISC_FEATURE
<223> OTHER INFORMATION: The sequence also may be obtained from Solanum
      tuberosum, Zeamayz L, Hordeum vulgare, or Brassica napus.

<400> SEQUENCE: 2

Leu Gly Glu Ser Leu
1               5

<210> SEQ ID NO 3
<211> LENGTH: 5
<212> TYPE: PRT
<213> ORGANISM: Triticum monococcum
```

```
<220> FEATURE:
<221> NAME/KEY: MISC_FEATURE
<223> OTHER INFORMATION: The sequence also may be obtained from Solanum
      tuberosum, Zeamayz L, Hordeum vulgare, or Brassica napus.

<400> SEQUENCE: 3

Val Gly Glu Leu Thr
1               5

<210> SEQ ID NO 4
<211> LENGTH: 5
<212> TYPE: PRT
<213> ORGANISM: Triticum monococcum
<220> FEATURE:
<221> NAME/KEY: MISC_FEATURE
<223> OTHER INFORMATION: The sequence also may be obtained from Solanum
      tuberosum, Zeamayz L, Hordeum vulgare, or Brassica napus.

<400> SEQUENCE: 4

Ile Gly Glu Leu Ser
1               5

<210> SEQ ID NO 5
<211> LENGTH: 5
<212> TYPE: PRT
<213> ORGANISM: Triticum monococcum
<220> FEATURE:
<221> NAME/KEY: MISC_FEATURE
<223> OTHER INFORMATION: The sequence also may be obtained from Solanum
      tuberosum, Zeamayz L, Hordeum vulgare, or Brassica napus.

<400> SEQUENCE: 5

Ala Gly Glu Leu Ser
1               5

<210> SEQ ID NO 6
<211> LENGTH: 5
<212> TYPE: PRT
<213> ORGANISM: Triticum monococcum
<220> FEATURE:
<221> NAME/KEY: MISC_FEATURE
<223> OTHER INFORMATION: The sequence also may be obtained from Solanum
      tuberosum, Zeamayz L, Hordeum vulgare, or Brassica napus.

<400> SEQUENCE: 6

Gly Glu Leu Thr Ile
1               5

<210> SEQ ID NO 7
<211> LENGTH: 4
<212> TYPE: PRT
<213> ORGANISM: Triticum monococcum
<220> FEATURE:
<221> NAME/KEY: MISC_FEATURE
<223> OTHER INFORMATION: The sequence also may be obtained from Solanum
      tuberosum, Zeamayz L, Hordeum vulgare, or Brassica napus.

<400> SEQUENCE: 7

Gly Glu Leu Ser
1
```

COSMETIC AND/OR PHARMACEUTICAL COMPOSITION COMPRISING A RELIEVING PEPTIDIC HYDROLYZATE

The present invention relates to the cosmetics and pharmaceuticals fields, and more particularly to the field of dermatology. The invention concerns a composition comprising, in a physiologically acceptable medium, a peptide hydrolyzate enriched in soothing bioactive peptide. The bioactive peptide is characterized in that it comprises 4 to 6 amino acids including at least one glycine residue, one leucine residue and one glutamic acid residue. Preferably, the active principle originates from the hydrolysis of proteins from plants selected from einkorn, potato, corn, barley and rapeseed. The invention also concerns the use of said peptide hydrolyzate, as an active principle in order to activate HMG-CoA reductase, in compositions intended to prevent or combat skin irritations. Finally, the invention concerns a cosmetic treatment method intended to prevent or combat skin irritations, in accordance with which an effective quantity of the peptide hydrolyzate, or a composition containing it, is applied to the zones to be treated.

The prime function of the epidermis is to constitute a barrier between the external environment and the internal medium. The outermost layer of the epidermis, the stratum corneum, is the entity which carries out this function. It is composed of keratinocytes in the final stage of their differentiation, as corneocytes, which are sealed off from each other by a thick intercellular lipid cement; it is both flexible and impermeable. This lipid cement contains cholesterol, a neutral lipid actively synthesized by the keratinocytes of the intermediate layers of the epidermis. The membrane enzyme which plays a key role in this synthesis is 3-hydroxy-3-methylglutaryl-Coenzyme A (HMG-CoA)-reductase (E.C. 1.1.1.34), which exists in at least two isoforms in the human skin (Luskey et al., J Biol Chem., 1985 260(18), p. 10271-7).

Following an abrupt alteration in the cutaneous barrier, a substantial and rapid increase in the synthesis of cholesterol is observed, associated with an increase in the expression and activity of HMG-CoA reductase (Menon G. K. et al., J. Lipid, Res., 1985, (26), p. 418-427). Furthermore, drug inhibition through the topical administration of statins confirms the importance of cholesterol in the epidermal barrier function and the central role of HMG-CoA reductase (Proksch E. et al., British J. Dermatol., 1993, (128), p. 473-482).

Many people suffer from symptoms linked to high skin sensitivity. That sensitivity usually results in blotchiness (erythemas), pain, tingling or pruritus, or even the appearance of reactive pimples. The causes of the appearance of said sensitivity are multiple but it is possible to distinguish sensitivities linked to stress, to the absorption of certain foods, to reactivity linked to climactic conditions or to secondary effects linked to the topical application of irritant products.

The majority of symptoms linked to skin sensitivity result from irritative processes which trigger localized cellular reactions resulting in the release of chemical mediators such as cytokines, substance P or prostaglandins. Skin irritation is generally accompanied by an alteration in the barrier function.

The principal aim of the present invention is to provide a soothing novel active principle which is capable of providing a solution to skin sensitivity.

In order to soothe the sensations of discomfort with sensitive skin, it is necessary on the one hand to limit the manifestations of the irritation, such as erythemas and tingling, by slowing down the release of cellular mediators of inflammation, and on the other hand to prevent the alteration or to re-establish the barrier function of the epidermis. In this particular field, the direct application of lipid substitutes such as ceramides (EP 1 272 148, US 2007/576937) or certain cholesterol derivatives (FR 2 789 312), has been widely described. In addition, the use of polyphenols to limit the release of inflammation mediators has also been described (WO/2004/058282). However, until now, no documents have either described or suggested the subject matter of the invention, i.e. a peptide hydrolyzate enriched in bioactive peptide in accordance with the invention may have advantageous properties in soothing sensitive skin and to prevent or combat skin irritations.

In a first aspect, the present invention concerns a cosmetic or pharmaceutical composition comprising, in a suitable physiological medium as a soothing active principle, a peptide hydrolyzate which is enriched in bioactive peptide which is capable of reinforcing the barrier function of the epidermis, characterized in that said bioactive peptide contains 4 to 6 amino acids including at least one glycine residue, one leucine residue and one glutamic acid residue. The inventors have in fact identified cosmetic activity in peptide hydrolyzates containing certain particular peptides, hereinafter termed bioactive peptides.

In particular, they have identified that, when applied to the skin, the peptide hydrolyzate enriched in bioactive peptide has soothing properties. These properties have been demonstrated by showing that the hydrolyzate, when applied to the skin, protects it from various experimental irritant agents.

The term "bioactive peptide" as used in the invention means a concatenation of at least four amino acids, bonded together via peptide linkages or by modified peptide linkages and which have in vivo or in vitro activity characteristic of the activity of the active principle of the invention.

The characteristic biological activity of the invention is defined in vitro by the capacity of the peptide to activate HMG-CoA reductase, either by increasing the protein synthesis of HMG-CoA reductase (by direct or indirect modulation of the genetic expression of HMG-CoA reductase), or by increasing the enzymatic activity of HMG-CoA reductase, or by other biological processes such as stabilisation of the HMG-CoA reductase protein or the stabilization of messenger RNA transcripts.

The term "skin" means the ensemble of covering tissues constituting the skin and mucous membranes, including the scalp.

The term "peptide hydrolyzate" means a mixture of compounds primarily represented by peptides or oligopeptides. In the invention, the terms "peptide hydrolyzate" or "active principle" will be used interchangeably.

The term "compounds of a peptide nature" means fragments of proteins, peptides and free amino acids present in the peptide hydrolyzate of the invention.

The term "topical application" means the fact of applying or smoothing the active principle of the invention, or a composition containing it, onto the surface of the skin or mucous membrane. The term "physiologically acceptable" means that the peptide hydrolyzate of the invention, or a composition containing it, is suitable for coming into contact with the skin or mucous membrane without causing toxic or intolerance reactions.

In accordance with a particularly advantageous implementation of the invention, the bioactive peptide contained in the hydrolyzate has a sequence with general formula (I):

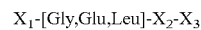

in which:
$X_1$ is alanine, valine, isoleucine or no amino acid,
$X_2$ is serine or threonine,
$X_3$ is leucine, isoleucine or no amino acid.

In accordance with a particularly preferred embodiment of the invention, the bioactive peptide has the following sequence:

```
                                        (SEQ ID No. 1)
        Ala-Glu-Gly-Leu-Ser-Ile (SEQ ID No. 2)
        Leu-Gly-Glu-Ser-Leu (SEQ ID No. 3)
        Val-Gly-Glu-Leu-Thr (SEQ ID No. 4)
        Ile-Gly-Glu-Leu-Ser (SEQ ID No. 5)
        Ala-Gly-Glu-Leu-Ser (SEQ ID No. 6)
        Gly-Glu-Leu-Thr-Ile (SEQ ID No. 7)
        Gly-Glu-Leu-Ser
```

In accordance with a particularly advantageous embodiment, the biologically active peptide corresponds to the sequence SEQ ID No. 5.

The active principle of the invention may be obtained by extraction from proteins of vegetable origin followed by controlled hydrolysis, which releases compounds with a peptide nature, including the bioactive peptides.

The use of peptide hydrolyzates, in particular peptide hydrolyzates with low molecular weights, has a number of advantages in cosmetics. In addition to the fact that compounds with a peptide nature are generated which did not exist in the starting protein mixture, hydrolysis and purification can be used to obtain more stable mixtures, which can be standardized more easily and do not cause allergic reactions in dermato-cosmetics.

It is also possible to use certain hydrolyzed extracts without purifying the compounds with a peptide nature corresponding to the bioactive peptides of the invention, but however, ensuring the presence of said peptides by appropriate analytical means.

Many proteins found in plants are likely to contain bioactive peptides in their structure. The hydrolysis carried out can be used to release said compounds of a particular peptide nature. It is possible, but not necessary to carrying out the invention, to initially extract either the proteins concerned and then to hydrolyse them, or to carry out hydrolysis initially on a crude extract and then to purify the compounds of a peptide nature.

In accordance with a preferred embodiment, said active principle derives from the hydrolysis of proteins from plants selected from einkorn, potato, corn, barley and rapeseed. Preferably, the plants used do not undergo prior fermentation.

Thus, the invention may be carried out using grains of engrain, or small einkorn (*Triticum monococcum*), which is a very ancient diploid wheat containing a particularly high level of proteins (Vallega 1992).

The invention may also be carried out using potato tubers from the genus Solanum and more particularly from the species *Solanum tuberosum*. The tuber does not belong to the root of the plant but to its buried stem from which thinner structures known as rhizomes branch out at the end of which the tubers are formed.

The invention may also be carried out using grain from one of many plants of the genus Zea, preferably the species *Zea mays* L. In accordance with the invention, the plant material used is the grain, preferably the grain freed from its envelope by carrying out a hulling step.

The invention may also be carried out using one of many plants from the Poaceae family, such as barley (*Hordeum vulgare* L.). In accordance with the invention, the plant material used is the grain, preferably the grain freed from its envelope by carrying out a hulling step.

The invention may also be carried out using grains of one of many plants from the crucifer family (Cruciferae or Brassicaceae). Examples of plants used in accordance with the invention belonging to this family that may be cited are oleaginous plants such as rapeseed (*Brassica napus*, var. *oleifera*). In accordance with the invention, the plant material used is the grain, preferably the grain freed from its envelope by carrying out a hulling step.

Any method for extraction or purification which is known to the skilled person may be used in order to prepare the hydrolyzate of the invention.

In a first step, the grains, or a specific portion of the plant (leaves, tubers, roots etc) are milled using a plant mill. The powder thus obtained may subsequently be "delipidized" using a conventional organic solvent (for example an alcohol, hexane or acetone).

Next, proteins are extracted using a modified conventional method (Osborne, 1924); the milled plant is taken up in suspension in an alkaline solution containing an adsorbent product of the insoluble polyvinylpolypyrrolidone (PVPP) type (0.01-20%); it has been observed that the hydrolysis operations and subsequent purification operations have been facilitated by this means. In particular, the concentration of phenol type substances, which interact with the proteins, are substantially reduced.

The soluble fraction containing proteins, glucides and possibly lipids is recovered after centrifuging and filtration steps. That crude solution is then hydrolyzed under managed conditions to generate the soluble peptides. Hydrolysis is defined as a chemical reaction involving cleavage of a molecule by water, that reaction possibly being carried out in a neutral, acidic or basic medium. In accordance with the invention, the hydrolysis is carried out chemically and/or advantageously using proteolytic enzymes. It is also possible to cite the use of endoproteases of plant origin (papain, bromain, ficain) and from micro-organisms (*Aspergillus, Rhizopus, Bacillus*, etc). The hydrolysis conditions are selected to promote enrichment in bioactive peptide.

For the same reasons as before, i.e. the elimination of polyphenolic substances, a quantity of polyvinylpolypyrrolidone is added to the reaction medium during this managed hydrolysis step. After filtration, to eliminate the enzymes and polymers, the filtrate (solution) obtained constitutes a first form of the active principle of the invention.

The hydrolyzate obtained at this stage may be purified further in order to select the low molecular weight fractions, preferably less than 6 kDa, and the peptides generated as a function of their nature. Fractionation may advantageously be carried out by successive ultrafiltration steps through filters with decreasing porosities, retaining the filtrates at each step and/or by a method of the chromatographic type, in order to specifically enrich the hydrolyzate in bioactive peptide.

Next, a phase for dilution in water or in any mixture containing water is carried out, followed by sterilization by ultrafiltration in order to obtain a peptide hydrolyzate characterized by a protein content of 0.5 to 5.5 g/l. This peptide hydrolyzate corresponds to the most purified form of the active principle of the invention.

The peptide hydrolyzate obtained in accordance with the invention is analyzed qualitatively and quantitatively using high pressure liquid chromatography (HPLC), in order to analyse the proteins with molecular weights of 0.2 to 2.5 kDa (using an appropriate solvent gradient). The various peptide fractions which are able to be isolated are then analyzed for their biological efficacy. These various fractions are then analyzed by mass spectrometry in order to specifically identify the amino acid content of the peptides of each peak. A sequencing analysis is also carried out in order to determine the peptide sequence of the bioactive peptide.

The hydrolyzate obtained is composed of peptides with a molecular weight of less than 6 kDa, preferably less than 6 kDa, and enriched in bioactive peptide containing 4 to 6 amino acids comprising at least one glycine residue, one leucine residue and one glutamic acid residue.

The effective quantity of active principle corresponds to the quantity necessary to obtain the desired result, namely to activate HMG-CoA reductase, to inhibit the production of cellular mediator of the interleukin-1 type, and thus to provide a soothing effect in individuals with sensitive skin. In accordance with certain aspects of the invention, the effective quantity of active principle is a sufficient quantity of peptide with general formula (I) to reduce or even eliminate a skin irritant effect. Thus, this quantity is variable as a function of the quantity and the nature of the compound with an irritant character used and/or of the sensitivity of the user of that compound.

In accordance with an advantageous embodiment of the invention, the active principle of the invention is present in the compositions of the invention in an effective quantity, i.e. in a concentration in the range approximately 0.0001% to 20%, and preferably in a concentration approximately in the range 0.05% to 5% with respect to the total final composition weight.

In accordance with an advantageous embodiment of the invention, the active principle of the invention is dissolved in one or more physiologically acceptable solvents conventionally used by the skilled person such as water, glycerol, ethanol, propylene glycol, butylene glycol, dipropylene glycol, ethoxylated or propoxylated diglycols, cyclic polyols, vaseline, a vegetable oil or any mixture of these solvents.

According to another advantageous embodiment of the invention, the active principle of the invention is initially dissolved in a cosmetic or pharmaceutical vector such as liposomes or adsorbed onto powdered organic polymers, mineral supports such as talcs or bentonites, and more generally dissolved in or fixed onto any physiologically acceptable vector.

The composition for use in accordance with the invention may in particular consist of a composition for hair care, in particular a shampoo, a conditioner, a medicated lotion, a mask, etc. Thus, the active principle of the invention could advantageously be used in anti-dandruff preparations for the scalp. The composition may also be in the form of a dye or mascara to be applied with a brush or a comb.

The composition for use in accordance with the invention could be applied by any appropriate means, in particular orally, parenterally or topically, and the formulation of the compositions will be adapted by the skilled person, in particular for cosmetic or dermatological compositions. Advantageously, the compositions of the invention are intended for topical administration. These compositions must therefore contain a physiologically acceptable medium, i.e. be compatible with the skin, the nails and the hair, and cover all cosmetic or dermatological forms.

Clearly, the active principle of the invention may be used alone or indeed in association with other active principles.

Advantageously, the compositions that may be used in accordance with the invention further contain various active principles intended to encourage the action of the active principle of the invention. Non-limiting examples of classes of ingredients which may be cited are as follows: other peptide active agents, plant extracts, healing agents, anti-ageing agents, anti-wrinkle agents, soothing agents, free radical scavengers, UV screens, agents stimulating the synthesis of dermal macromolecules or energy metabolism, moisturizers, antibacterial agents, antifungal agents, anti-inflammatory agents, anaesthetics, agents modulating skin differentiation or pigmentation or skin depigmentation, and agents stimulating the growth of the nails or hair. Preferably, a free radical scavenger or antioxidizing agent is used.

In accordance with one aspect of the invention, the compositions may further comprise active principles with a secondary irritant effect which are therefore likely to cause skin irritation, especially in individuals with sensitive skin. Examples of active principles which are likely to have a secondary irritant effect which may be cited are: keratolytic agents such as alpha-hydroxy-acids such as glycolic, lactic, malic, citric, tartaric, mandelic acid and their derivatives; ss-hydroxy acids such as salicylic acid and its derivatives; alpha-keto-acids such as ascorbic acid or vitamin C and its derivatives; retinoids such as retinol and its esters, retinal, retinoic acid and its derivatives; minoxidil and its derivatives; lithium salts; hair dyes or colouring agents such as para-phenylene diamine (p-PDA) and certain of its derivatives such as N-phenyl p-PDA and toluene 2,5-diamine sulphate; meta-phenylene diamine (m-PDA) and certain of its derivatives such as toluene 3,4-diamine; ortho-phenylene diamine (o-PDA); fragrancing alcoholic solutions (fragrances, toilet water, after-shave, deodorants); antiperspirants (certain aluminum salts); depilatory active ingredients or active ingredients for permanent waves (thiols, ammonia); depigmenting agents (hydroquinone); head lice treatment agents; detergents (ionic and non-ionic); and mixtures thereof Thus, in accordance with this aspect of the invention, the peptide hydrolyzate of the invention will be used as an active principle to prevent or combat skin irritation caused by the irritant active principle.

Clearly, the invention is aimed at mammals in general, and more particularly at human beings.

These compositions may in particular be in the form of an aqueous, hydro-alcoholic or oily solution; an oil-in-water, water-in-oil or multiple emulsion; they may also be in the form of creams, suspensions, or powders, adapted to application to the skin, the mucous membranes, the lips and/or the nails and the hair. These compositions may also be fluid to a greater or lesser extent and have the appearance of a cream, lotion, milk, serum, pomade, gel, paste or a foam. They may also be in the solid form, such as a stick, or be applied to the skin in the form of an aerosol. They may be used as a toiletry and/or as a skin makeup product.

This set of compositions further includes any additive generally used in the envisaged field of the application as well as the adjuvants necessary for their formulation such as solvents, thickening agents, diluents, anti-oxidizing agents, colorants, sun screens, self-tanning agents, pigments, fillers, preservatives, fragrances, odour absorbers, other cosmetic active principles, essential oils, vitamins, essential fatty acids, surfactants, film-forming polymers, etc.

In all cases, the skilled person will ensure that these adjuvants as well as their proportions are selected so that they do not have a deleterious effect on the desired advantageous properties of the composition of the invention. These adjuvants may, for example, correspond to concentrations of 0.01% to 20% of the total composition weight. When the composition of the invention is an emulsion, the fatty phase may represent 5% to 80% by weight, preferably 5% to 50% by weight with respect to the total composition weight. The emulsifiers and co-emulsifiers used in the composition will be selected from those in conventional use in the field under consideration. As an example, they may be used in a proportion of 0.3% to 30% by weight, with respect to the total composition weight.

In a second aspect, the subject matter of the invention concerns the use, in a cosmetic composition, of an effective quantity of peptide hydrolyzate as an active principle activating human HMG-CoA reductase.

Thus, because of its particular properties, said active principle could be used in a cosmetic composition intended to soothe sensitive skin.

In accordance with a further aspect of the invention, the peptide hydrolyzate could advantageously be used as the active principle in a cosmetic composition intended to protect the skin against external challenges.

The expression "external challenges" means challenges that may originate from the environment. Examples which may be cited are challenges such as pollution, UV (ultraviolet radiation), oxidizing agents, or products with an irritant nature such as surfactants, preservatives, fragrances, or certain active principles used in dermato-cosmetology such as keratolytic active ingredients, exfoliants, alpha-hydroxy acids (in particular lactic, glycolic, citric acids), 3-hydroxy acids (especially salicylic, n-octanoyl-5-salicylic acids) and retinoids (especially retinol and its esters), and active ingredients for treating head lice. It is also possible to cite mechanical challenges, such as abrasion, shaving or depilation. Extreme climactic conditions are also a major cause of skin challenges. These external challenges result in an alteration in the barrier function which manifests itself in skin discomfort, disagreeable sensorial phenomena such as tightness or itching, or even excessive weakness and blotchiness.

In particular, the invention pertains to the use of the hydrolyzate of the invention in a cosmetic composition intended to prevent or treat damage caused to the skin by UV radiation.

In particular, the invention concerns the use of the hydrolyzate of the invention in a cosmetic composition intended to prevent or treat damage caused to the skin by oxidizing agents.

In particular, the invention provides for the use of the hydrolyzate of the invention in a cosmetic composition intended to prevent or treat damage caused to the skin by external challenges to the skin selected from mechanical treatments such as shaving or depilation, too-intense degreasing of the skin by detergents, extreme climactic conditions or abrupt variations in temperature and humidity.

In a third aspect, the invention pertains to the use of an effective quantity of peptide hydrolyzate of the invention to prepare a pharmaceutical composition intended to prevent or treat skin inflammation, such as erythemas, in particular due to ultraviolet radiation, pruritus, hives, insect bites, allergies, or alopecia in its inflammatory phases.

In this form of the invention, the compositions will be appropriate for oral administration for pharmaceutical use. Thus, the compositions could in particular be in the form of tablets, capsules, gelules, chewing gum, powder for consumption as they are or for contemporaneous mixing with a liquid, a syrup, gel or any other form known to the skilled person. These compositions also include any additive routinely used in the envisaged field of application such as the adjuvants necessary for their formulation such as solvents, thickening agents, diluents, antioxidants, preservatives, other pharmaceutical active principles, essential oils, vitamins, essential fatty acids, etc.

In a fourth aspect, the invention concerns a cosmetic treatment method intended to reduce or eliminate the secondary irritant effect of an active principle present in a cosmetic composition, characterized in that a composition comprising an effective quantity of peptide hydrolyzate is applied topically to the skin.

Particular implementations of this cosmetic treatment method also emerge from the above description. Other advantages and characteristics of the invention will become apparent from the following non-limiting examples given by way of illustration.

LIST OF FIGURES

FIG. 1: An example of a chromatogram obtained by HPLC, identifying the peak corresponding to the bioactive peptide in a hydrolyzate from einkorn;

FIG. 2: An example of a chromatogram obtained by HPLC, identifying the peak corresponding to the bioactive peptide in a hydrolyzate from potato;

FIG. 3: An example of a chromatogram obtained by HPLC, identifying the peak corresponding to the bioactive peptide in a hydrolyzate from corn.

EXAMPLE 1

Preparation of a Peptide Hydrolyzate from Einkorn (*Triticum monococcum*)

Grains of einkorn (*Triticum monococcum*) were dissolved in 10 volumes of water in the presence of 2% of POLYCLAR® 10 (polyvinylpyrrolidone—PVPP—insoluble). The mixture was adjusted to a pH in the range 6 to 8 with an aqueous 1M solution of sodium hydroxide.

After adjusting the pH, an amylase (Hasidase®) and a protease (papain, 2%) were added to the reaction medium. Hydrolysis was complete after 2 hours mixing at 50° C. Next, the enzyme was inactivated by heating the solution to 80° C. for 2 hours. After centrifuging, the supernatant aqueous solution corresponding to a crude einkorn hydrolyzate was recovered. The hydrolysis conditions had been selected so as to allow an enrichment in bioactive peptide containing 4 to 6 amino acids containing the residues Gly, Leu and glutamic acid.

The method for the purification of the crude hydrolyzate commenced with successive filtrations using Seitz-Orion filter plates with decreasing porosity (to 0.2 μm) in order to obtain a bright, clear solution termed hydrolyzate 1.

In this step, the einkorn hydrolyzate 1 was characterized by a clear yellow colour and by a dry extract assaying at 20 to 25 g/kg, a protein content of 10 to 12 g/l and a sugar content of 5 to 8 g/l.

The protein nature of hydrolyzate 1 was identified after electrophoretic analysis on NuPAGE® Bis-Tris Pre-cast polyacrylamide gel (Invitrogen). The einkorn protein hydrolyzate was heated to 70° C. for 10 minutes under reducing denaturing conditions in a NuPAGE® LDS sample preparation buffer. A solution of NuPAGE® antioxidizing agent was added to the internal cell (cathode) to prevent the reduced proteins from re-oxidizing during electrophoresis. Protein migration was carried out in a NuPAGE® MES migration buffer with the standard SeeBlue Plus2 as a molecular weight marker. Protein staining was carried out using Coomassie Blue® R-250. Under these conditions, a band was observed at 24 kDa, corresponding to the enzyme, then smaller proteins at 6 kDa.

Hydrolyzate 1 was then purified by ultrafiltration using a Pellicon® 2 Biomax 5 kDa cassette in order to eliminate all traces of enzymes. At the end of purification, a yellow-or-angey peptide hydrolyzate was obtained which was bright and clear. A dilution phase was then carried out to obtain a peptide hydrolyzate characterized by a protein content of 1.5 to 3.5 g/l. This peptide hydrolyzate corresponded to the active principle of the invention.

This peptide hydrolyzate was then analyzed using high pressure liquid chromatography (HPLC) with the aid of a HP 1100 apparatus controlled using ChemStation software. The column used during elution of the hydrolyzate was a Nucleosil® 300-5 C4 MPN (125×4 mn) column which allowed proteins with molecular weights of 0.2 to 25 kDa to be chromatographed under the following conditions:

Acetonitrile gradient
Uptisphere OPB 125×3 mm column
solvent A: HPLC grade water containing 0.1% trifluoroacetic acid (TFA)
solvent B: acetonitrile
gradient: 100% to 15% solvent A in 35 min Under these chromatographic conditions, several peptide fractions were able to be isolated. An example of a chromatogram obtained by HPLC (high pressure liquid chromatography) identifying a peak corresponding to the bioactive peptide is given in FIG. 1.

These various fractions were then analyzed by mass spectrometry in order to specifically identify the amino acid content of the peptides of each peak. Sequencing analysis was also carried out in order to determine the peptide sequence of the bioactive peptide.

The amino acid composition of the active principle of the invention was also determined. It was carried out after acid hydrolysis and identification by high pressure liquid chromatography using PICT (phenylisothiocyanate) pre-column derivatization.

An example of the amino acid composition of the hydrolyzate is given in the following table (in %):

| Amino acids | % |
|---|---|
| Alanine | 3.1 |
| Aspartic Acid | 4.7 |
| Arginine | 3.1 |
| Glutamic Acid | 32.8 |
| Glycine | 3.1 |
| Histidine | <3.0 |
| Isoleucine | <5.5 |
| Leucine | 6.2 |
| Lysine | <2.2 |
| Phenylalanine | 4.5 |
| Proline | 10.9 |
| Serine | 4.7 |
| Threonine | 3.1 |
| Tyrosine | <3.6 |
| Valine | 4.7 |
| Tryptophan | <1.5 |

EXAMPLE 2

Preparation of a Peptide Hydrolyzate from Tubers Belonging to the Species *Solanum tuberosum*

Potato tubers (*Solanum tuberosum*) were dissolved in 10 volumes of water in the presence of 2% of POLYCLAR® 10 (polyvinylpyrrolidone—PVPP—insoluble). The mixture was adjusted to a pH in the range 6 to 8 with an aqueous 1M solution of sodium hydroxide. Precipitation in acid medium was then carried out. The sediment was taken up into solution and after adjusting the pH, 2% papain was added to the reaction medium. The hydrolysis was complete after 2 hours mixing at 55° C. Next, the enzyme was inactivated by heating the solution to 80° C. for 2 hours. After centrifuging, the supernatant aqueous solution corresponding to a crude potato hydrolyzate was recovered. The hydrolysis conditions had been selected so as to allow an enrichment in bioactive peptide containing 4 to 6 amino acids containing the residues Gly, Leu and glutamic acid.

The method for the purification of the crude hydrolyzate commenced with successive filtrations using Seitz-Orion filter plates with decreasing porosity (to 0.2 μm) in order to obtain a bright, clear yellow solution termed hydrolyzate 1.

In this step, the potato hydrolyzate 1 was characterized by a dry extract assaying at 40 to 60 g/kg, a protein content of 20 to 25 g/l and a sugar content of 1 to 3 g/l.

The protein nature of hydrolyzate 1 was identified after electrophoretic analysis on NuPAGE® Bis-Tris Pre-cast polyacrylamide gel (Invitrogen). The potato protein hydrolyzate was heated to 70° C. for 10 minutes under reducing denaturing conditions in a NuPAGE® LDS sample preparation buffer. A solution of NuPAGE® antioxidizing agent was added to the internal cell (cathode) to prevent the reduced proteins from re-oxidizing during electrophoresis. Protein migration was carried out in a NuPAGE® MES migration buffer with the standard SeeBlue Plus2 as a molecular weight marker. Protein staining was carried out using Coomassie Blue® R-250. Under these conditions, it was observed that the proteins obtained had a molecular weight of less than 6 kDa.

Hydrolyzate 1 was then purified by ultrafiltration in order to retain only peptides with a molecular weight of less than 5 kDa using tangential flow filtration. To this end, hydrolyzate 1 was pumped under pressure through a Pellicon® support equipped with a Pellicon® 2 Biomax 5 kDa cassette. At the end of purification, a bright, clear peptide hydrolyzate was obtained. A dilution phase was then carried out to obtain a peptide hydrolyzate characterized by a protein content of 3.5 to 5.5 g/l. This peptide hydrolyzate corresponded to the active principle of the invention.

This peptide hydrolyzate was then analyzed using high pressure liquid chromatography (HPLC) with the aid of a HP 1100 apparatus controlled using ChemStation software. The column used during elution of the hydrolyzate was a Nucleosil® 300-5 C4 MPN (125×4 mn) column which allowed proteins with molecular weights of 0.2 to 25 kDa to be chromatographed (under conditions identical to Example 1). Under these chromatographic conditions, several peptide fractions were able to be isolated.

These various fractions were then analyzed by mass spectrometry in order to specifically identify the amino acid content of the peptides of each peak. Sequencing analysis was also carried out in order to determine the peptide sequence of the bioactive peptide.

An example of a chromatogram obtained by HPLC (high pressure liquid chromatography) identifying a peak corresponding to the bioactive peptide is given in FIG. 2.

The amino acid composition of the active principle of the invention was also determined. It was carried out after acid hydrolysis and identification by high pressure liquid chromatography using PICT (phenylisothiocyanate) pre-column derivatization.

An example of the amino acid composition of the hydrolyzate is given in the table below (as a %):

| Amino acids | % |
|---|---|
| Alanine | 7.8 |
| Aspartic Acid | 20.1 |
| Arginine | 7.3 |
| Glutamic Acid | 17.4 |
| Glycine | 7.3 |
| Histidine | 3.2 |
| Isoleucine | 9.1 |
| Leucine | 15.1 |
| Lysine | 11.4 |
| Phenylalanine | 8.7 |
| Proline | 7.7 |
| Serine | 8.7 |
| Threonine | 9.1 |
| Tyrosine | 8.2 |
| Valine | 10.5 |
| Tryptophan | 1.4 |

EXAMPLE 3

Preparation of a Peptide Hydrolyzate from Corn Meal (*Zea mays* L.)

The corn meal (*Zea mays* L.) was dissolved in 10 volumes of water in the presence of 2% of POLYCLAR® 10 (polyvinylpyrrolidone—PVPP—insoluble). The mixture was adjusted to a pH in the range 6 to 8 with an aqueous 1M solution of sodium hydroxide.

After adjusting the pH, 2% papain was added to the reaction medium. Hydrolysis was complete after 2 hours mixing at 55° C. Next, the enzyme was inactivated by heating the solution a 80° C. for 2 hours. After centrifuging, the supernatant aqueous solution corresponding to crude corn hydrolyzate was recovered. The hydrolysis conditions had been selected so as to allow an enrichment in bioactive peptide containing 4 to 6 amino acids containing the residues Gly, Leu and glutamic acid.

The method for the purification of the crude hydrolyzate commenced with successive filtrations using Seitz-Orion filter plates with decreasing porosity (to 0.2 μm) in order to obtain a bright, clear yellow solution termed hydrolyzate 1.

In this step, the corn hydrolyzate 1 was characterized by a dry extract assaying at 20 to 30 g/kg, a protein content of 20 to 25 g/l and a sugar content of 2 to 5 g/l.

The protein nature of hydrolyzate 1 was identified after electrophoretic analysis on NuPAGE® Bis-Tris Pre-cast polyacrylamide gel (Invitrogen). The corn protein hydrolyzate was heated to 70° C. for 10 minutes under reducing denaturing conditions in a NuPAGE® LDS sample preparation buffer. A solution of NuPAGE® antioxidizing agent was added to the internal cell (cathode) to prevent the reduced proteins from re-oxidizing during electrophoresis. Protein migration was carried out in a NuPAGE® MES migration buffer with the standard SeeBlue Plus2 as a molecular weight marker. Protein staining was carried out using Coomassie Blue® R-250. Under these conditions, it was observed that the proteins obtained had a molecular weight of less than 6 kDa.

Hydrolyzate 1 was then purified by ultrafiltration with a Pellicon® 2 Biomax 5 kDa cassette to eliminate high molecular weight proteins and retain only compounds of a peptide nature that were less than 5 kDa.

After this final purification, a dilution phase was carried out to obtain a peptide hydrolyzate characterized by a protein content in the range 3.5 to 5.5 g/l. This peptide hydrolyzate corresponded to the active principle of the invention.

This peptide hydrolyzate was then analyzed using high pressure liquid chromatography (HPLC) with the aid of a HP 1100 apparatus controlled using ChemStation software. The column used during elution of the hydrolyzate was a Nucleosil® 300-5 C4 MPN (125×4 mn) column which allowed proteins with molecular weights of 0.2 to 25 kDa to be chromatographed (with an appropriate solvent gradient identical to Example 1). Under these chromatographic conditions, several peptide fractions were able to be isolated.

An example of a chromatogram obtained by HPLC (high pressure liquid chromatography) identifying a peak corresponding to the bioactive peptide is given in FIG. 3.

These various fractions were then analyzed by mass spectrometry in order to specifically identify the amino acid content of the peptides of each peak. Sequencing analysis was also carried out in order to determine the peptide sequence of the bioactive peptide.

The amino acid composition of the active principle of the invention was also determined. It was carried out after acid hydrolysis and identification by high pressure liquid chromatography using PICT (phenylisothiocyanate) pre-column derivatization. An example of the amino acid composition of the hydrolyzate is given in the table below (as a %):

| Amino acids | % |
|---|---|
| Alanine | 9.4 |
| Aspartic Acid | 7.2 |
| Arginine | 3.6 |
| Glutamic Acid | 23.7 |
| Glycine | 3.6 |
| Histidine | 2.2 |
| Isoleucine | 4.5 |
| Leucine | 16.1 |
| Lysine | 2.2 |
| Phenylalanine | 6.7 |
| Proline | 10.3 |
| Serine | 6.3 |
| Threonine | 4.0 |
| Tyrosine | 5.8 |
| Valine | 5.4 |
| Tryptophan | <0.5 |

EXAMPLE 4

Preparation of a Peptide Hydrolyzate from Barley (*Hordeum vulgare* L.)

Barley flour (*Hordeum vulgare* L) was prepared in conventional manner by milling and screening the grain after separating it from its envelope. It was dissolved in 20 volumes of water in the presence of 2% of POLYCLAR® 10 (polyvinylpyrrolidone—PVPP—insoluble). The mixture was adjusted to a pH in the range 6 to 7.5 with an aqueous 1M solution of sodium hydroxide.

After adjusting the pH, 2% bromelain was added to the reaction medium. Hydrolysis was complete after 2 hours mixing at 50° C. The enzyme was inactivated by heating the solution to 80° C. for 2 hours. After centrifuging, the aqueous solution corresponding to the barley extract was recovered.

In order to eliminate as much sugar as possible deriving from the degradation of cellulose, another extraction pathway is also possible. The barley was dissolved in 10 volumes of water and the pH of the solution was adjusted to between 4 and 5 with a 1M hydrochloric acid solution. After adjusting the pH, 2% alpha-amylase was added to the reaction medium. Hydrolysis was complete after mixing for 2 hours at 50° C. At the end of the reaction, the reaction mixture was filtered and the residue from the extraction was recovered. This latter was then dissolved in 10 volumes of water in the presence of 2%

POLYCLAR® 10 (polyvinylpyrrolidone—PVPP—insoluble). The pH was then adjusted to between 6 and 7.5 with an aqueous 1M solution of sodium hydroxide.

After adjusting the pH, 2% bromelain was added to the reaction medium. Hydrolysis was complete after 2 hours mixing at 50° C. The enzyme was inactivated by heating the solution to 80° C. for 2 hours. After centrifuging, the aqueous solution corresponding to a first form of the barley hydrolyzate was recovered. The hydrolysis conditions had been selected so as to allow an enrichment in bioactive peptide containing 3 to 5 amino acids containing the residues Gly and Lys.

The method for the purification of the crude hydrolyzate commenced with successive filtrations using Seitz-Orion filter plates with decreasing porosity (to 0.2 µm) in order to obtain a bright, clear solution. In this step, the barley hydrolyzate was characterized by a dry weight of 10 to 13 g/kg, a protein content of 5 to 7 g/l and a sugar content of 4 to 6 g/l.

The protein nature of this extract was identified by electrophoresis on polyacrylamide gel. For this analysis, NuPAGE® Bis-Tris 4-12% (Invitrogen) gels were used. The barley protein hydrolyzate was heated to 70° C. for 10 minutes under reducing denaturing conditions in a NuPAGE® LDS sample preparation buffer. A solution of NuPAGE® antioxidizing agent was added to the internal cell (cathode) to prevent the reduced proteins from re-oxidizing during electrophoresis. Protein migration was carried out in a NuPAGE® MES migration buffer with the Mark 12 and Sharp standards (Invitrogen) as molecular weight markers. Protein staining was carried out using the SilverXpress® staining kit (Invitrogen). Under these conditions, proteins were observed with a molecular weight in the range 85 kDa to 5 kDa or less (detection limit).

This form of the hydrolyzate was then purified by eliminating the high molecular weight proteins by means of tangential flow filtration.

To this end, the barley solution was pumped under pressure through a Pellicon® support provided with a Pellicon® 2 Biomax 100 kDa cassette. This first filtrate was recovered for subsequent filtration through a second Pellicon® 2 Biomax 50 kDa cassette. A second filtrate was then recovered which was eluted through a Pellicon® 2 Biomax 30 kDa cassette. The third filtrate was then eluted on a Pellicon® 2 Biomax 10 kDa cassette. Finally, this was recovered and re-concentrated using a Pellicon® 2 Biomax 3 kDa cassette. At the end of purification, a barley peptide hydrolyzate was obtained which was beige in colour, bright and clear. It was characterized by a dry weight of 6 to 8 g/kg, a protein content of 5 to 7 g/l and a sugar concentration of less than 1 g/l.

After this final purification, a dilution phase was carried out in order to obtain a peptide hydrolyzate characterized by a protein content in the range 3.5 to 5.5 g/l. This peptide hydrolyzate corresponded to the active principle of the invention.

This peptide hydrolyzate was then analyzed using high pressure liquid chromatography (HPLC) with the aid of a HP 1100 apparatus controlled using ChemStation software. The column used during elution of the hydrolyzate was a Nucleosil® 300-5 C4 MPN (125×4 mn) column which allowed proteins with molecular weights of 0.2 to 25 kDa to be chromatographed (under conditions identical to Example 1). Under these chromatographic conditions, several peptide fractions were able to be isolated.

The amino acid composition of the active principle of the invention was also determined. It was carried out after acid hydrolysis and identification by high pressure liquid chromatography using PICT (phenylisothiocyanate) pre-column derivatization.

EXAMPLE 5

Preparation of a Peptide Hydrolyzate from Rapeseed Meal (*Brassica napus*, var. *oleifera*)

Rapeseed meal (*Brassica napus*) was dissolved in 10 volumes of water in the presence of 2% of POLYCLAR® 10 (polyvinylpyrrolidone—PVPP—insoluble). The mixture was adjusted to a pH in the range 6 to 8 with an aqueous 1M solution of sodium hydroxide.

After adjusting the pH, 2% bromelain was added to the reaction medium. Hydrolysis was complete after 2 hours mixing at 55° C. Next, the enzyme was inactivated by heating the solution to 80° C. for 2 hours. After centrifuging, the supernatant aqueous solution corresponding to a crude rapeseed hydrolyzate was recovered. The hydrolysis conditions had been selected so as to allow an enrichment in bioactive peptides containing 3 to 5 amino acids containing the residues Gly and Lys.

The method for the purification of the crude hydrolyzate commenced with successive filtrations using Seitz-Orion filter plates with decreasing porosity (to 0.2 µm) in order to obtain a bright, clear solution termed hydrolyzate 1.

In this step, the rapeseed hydrolyzate 1 was characterized by a dry extract assaying at 30 to 40 g/kg, a protein content of 25 to 35 g/l and a sugar content of 2 to 5 g/l.

The protein nature of hydrolyzate 1 was identified after electrophoretic analysis on NuPAGE® Bis-Tris Pre-cast polyacrylamide gel (Invitrogen). The rapeseed protein hydrolyzate was heated to 70° C. for 10 minutes under reducing denaturing conditions in a NuPAGE® LDS sample preparation buffer. A solution of NuPAGE® antioxidizing agent was added to the internal cell (cathode) to prevent the reduced proteins from re-oxidizing during electrophoresis. Protein migration was carried out in a NuPAGE® MES migration buffer with the standard SeeBlue Plus2 as a molecular weight marker. Protein staining was carried out using Coomassie Blue® R-250. Under these conditions, 3 major families of proteins were observed: the first family corresponded to proteins with a molecular weight of 65 to 35 kDa, the second family corresponded to 25 to 15 kDa proteins and the final family to proteins with a molecular weight of less than 5 kDa.

Hydrolyzate 1 was then purified by eliminating the high molecular weight proteins by means of tangential flow filtration. To this end, hydrolyzate 1 was pumped under pressure through a Pellicon® support provided with a Pellicon® 2 Biomax 50 kDa cassette. This first filtrate was recovered for subsequent filtration through a second Pellicon® 2 Biomax 10 kDa cassette. A second filtrate was then recovered which was eluted through a final Pellicon® 2 Biomax 5 kDa cassette. At the end of purification, a yellow-orangey, bright and clear peptide hydrolyzate was obtained. A dilution phase was carried out in order to obtain a peptide hydrolyzate characterized by a dry extract assaying at 6 to 8 g/kg, a protein content of 3.5 to 6 g/l and a sugar concentration of 1 to 2 g/l. This peptide hydrolyzate corresponded to the active principle of the invention.

This peptide hydrolyzate was then analyzed using high pressure liquid chromatography (HPLC) with the aid of a HP 1100 apparatus controlled using ChemStation software. The column used during elution of the hydrolyzate was a Nucleosil® 300-5 C4 MPN (125×4 mn) column which allowed proteins with molecular weights of 0.2 to 25 kDa to be chromatographed (under conditions identical to Example 1). Under these chromatographic conditions, several peptide fractions were able to be isolated.

The amino acid composition of the active principle of the invention was also determined. It was carried out after acid hydrolysis and identification by high pressure liquid chromatography using PICT (phenylisothiocyanate) pre-column derivatization.

EXAMPLE 6

Study of the Protective Effect of the Hydrolyzate of Example 1 on Skin Cells Subjected to Oxidative Stress The aim of this study was to determine the protective effect of the hydrolyzate of Example 1 in a concentration of 0.5% with respect to normal human keratinocytes subjected to oxidative stress caused by hydrogen peroxide ($H_2O_2$) in a concentration of 2 mM. To this end, cell viability tests were carried out using the MTT technique.

Protocol: Normal human keratinocytes were treated with the hydrolyzate of Example 1, 0.5%, for 24 hours, subjected to oxidative stress caused by 2 mM $H_2O_2$ for 30 minutes, then cultivated for a further 24 hours in the presence of the same concentration of the hydrolyzate of Example 1. Controls which had not been treated with the peptide were run under the same conditions. At the end of the experiment, the cells were incubated in a solution containing 0.1 mg/ml of MTT (3-[4,5-dimethylthiazol-2-yl]-2,5-diphenyltetrazolium, bromide). This compound is absorbed by living cells then metabolized by mitochondrial enzymes to a blue-violet compound, formazan, which can be assayed by spectrophotometry at 540 nm. The optical density (O.D.) is directly proportional to the mitochondrial enzyme activity and to the number of living cells.

Results:
The cell viability evaluation using the MTT technique showed that the hydrolyzate of Example 1 in a concentration of 0.5% substantially increased the cell viability of normal human keratinocytes.

Conclusion:
The hydrolyzate of Example 1 effectively protects skin cells against the cytotoxic effects of oxidative stress.

EXAMPLE 7

Study of the Protective Effect of the Hydrolyzate of Example 2 on Skin Cells Challenged by a Detergent The aim of this study was to determine the protective effect of the hydrolyzate of Example 2 with respect to normal human keratinocytes challenged by a detergent, in particular SDS. To this end, cell viability tests were carried out using the MTT technique.

Protocol:
Normal human keratinocytes were treated with the hydrolyzate of Example 2, 0.5%, for 24 hours, then brought into contact with 15 µg/ml SDS for 24 hours in the presence of the same concentration of the hydrolyzate of Example 2. Controls which had not been treated with the peptide were run under the same conditions. At the end of the experiment, the cells were incubated in a solution containing 0.1 mg/ml of MTT (3-[4,5-dimethylthiazol-2-yl]-2,5-diphenyltetrazolium, bromide) following the protocol described in Example 6.

Results:
The cell viability evaluation using the MTT technique showed that the hydrolyzate of Example 2 in a concentration of 0.5% substantially increased the cell viability of normal human keratinocytes.

Conclusion:
The hydrolyzate of Example 2 effectively protects skin cells against a challenge by an SDS type detergent.

EXAMPLE 8

Ex Vivo Study of the Effect of the Hydrolyzate of Example 2 on the Secretion of Interleukin-I (IL-1 Alpha) by Human Skin Biopsies The aim of this study was to determine the ex vivo effect of the hydrolyzate of Example 2 on the production of the cell mediator of inflammation, IL-1 alpha, by human skin biopsies cultivated under standard conditions or subjected to a stress by UVB radiation or SDS.

Protocol:
5 mm diameter human skin biopsies were cultured at the air-liquid interface in the presence of standard culture medium. The samples were treated with the hydrolyzate of Example 2 in a concentration of 0.5% for 24 hours then irradiated with UVB (200 mJ/cm$^2$) and cultured again for 24 hours or placed in contact with SDS, 2.5%, for 24 hours, in the presence of the same concentration of the hydrolyzate of Example 2. Controls which had not been treated with the peptide were run under the same conditions. At the end of the experiment, the quantity of interleukin-1 alpha released into the culture medium was assayed using the ELISA technique.

Results:
The quantity of IL-1 alpha released by the skin biopsies after a UVB or SDS stress was reduced if the samples had been treated with the hydrolyzate of Example 2.

Conclusion:
The hydrolyzate of Example 2 substantially reduces the inflammation induced by UBV or the detergent SDS.

EXAMPLE 9

Study of the Protective Effect of the Hydrolyzate of Example 2 on Skin Cells Subjected to Ultraviolet Radiation (UVB)

The aim of this study was to determine the protective effect of the hydrolyzate of Example 2 with respect to normal human keratinocytes subjected to stress by UVB radiation. To this end, cell viability tests were carried out using the MTT technique.

Protocol:
Normal human keratinocytes were treated with the hydrolyzate of Example 2, 0.5%, for 24 hours, irradiated with UVB (50 mJ/cm$^2$) then cultivated for a further 24 hours in the presence of the same concentration of the hydrolyzate of Example 2. Controls which had not been treated and irradiated were run under the same conditions. At the end of the experiment, the cells were incubated in a solution containing 0.1 mg/ml of MTT (3-[4,5-dimethylthiazol-2-yl]-2,5-diphenyltetrazolium, bromide) and the MTT was assayed by means of the protocol described in Example 6.

Results:
The cell viability evaluation using the MTT technique showed that the hydrolyzate of Example 2 in a concentration of 0.5% substantially increased the cell viability after irradiation with UVB.

Conclusion:
The hydrolyzate of Example 2 increases the cell viability and effectively protects skin cells against the cytotoxic effects of UVB radiation.

EXAMPLE 10

Study of the Expression of HMG-CoA Reductase in Skin Biopsies in the Presence of the Hydrolyzate of Example 1

The aim of this study was to determine the influence of the hydrolyzate of Example 1 in a concentration of 1% on the expression of HMG-CoA reductase.

Protocol:
Human skin samples were cultured at the air/liquid interface. The hydrolyzate of Example 1, 1%, was applied topically then the samples were incubated for 24 hours or 48 hours.

These skin samples were then fixed with formaldehyde then included into paraffin. 2 to 3 µm sections were then produced. Immunoassay was carried out after retrieving specific sites by microwave treatment then incubating in trypsin. The immunoassay was carried out using a rabbit polyclonal antibody specific for HMG-CoA reductase (Upstate, Millipore), then a secondary antibody coupled with a fluorescent marker. The skin sections were then examined using an Epi-fluorescence microscope (Nikon Eclipse E600 microscope).

Results:

The microscopic observations indicated stronger fluorescence in the upper layers of the epidermis of skin treated with the hydrolyzate of Example 1 in a concentration of 1% compared with the untreated control.

Conclusion:

The hydrolyzate of Example 1 stimulates the expression of HMG-CoA reductase in the upper layers of the epidermis.

EXAMPLE 11

Study of the Expression of HMG-CoA Reductase in Normal Human Keratinocytes, in the Presence of the Hydrolyzate of Example 2

The aim of this study was to determine the influence of the hydrolyzate of Example 2 on the expression of HMG-CoA reductase in normal human keratinocytes.

Protocol:

Cultured normal human keratinocytes were treated with the hydrolyzate of Example 2 in a concentration of 0.5% for 24 or 48 hours (the medium containing the active ingredient was changed every 24 hours). The cells were then washed, and fixed with cold methanol for 4 minutes at 4° C. The cells were incubated in the presence of a rabbit polyclonal antibody specific for HMG-CoA reductase (Upstate, Millipore), then a secondary antibody coupled with a fluorescent marker. The cells were then examined using an Epi-fluorescence microscope (Nikon Eclipse E600 microscope).

Results:

The microscopic observations indicated more intense cytoplasmic fluorescence in the cells treated with the hydrolyzate of Example 2 in a concentration of 0.5%.

Conclusion:

The hydrolyzate of Example 2 stimulates the expression of HMG-CoA reductase in normal human keratinocytes.

EXAMPLE 12

Preparation of Compositions

1—Sunscreen Cream:

| Commercial names | INCI names | % by weight |
|---|---|---|
| PHASE A | | |
| Demineralized water | Aqua (Water) | qsp |
| Pemulen TR1 | Acrylates/C10-30 Alkyl Acrylate Crosspolymer | 0.40 |
| Glycerin | Glycerin | 3.00 |
| Nipastat Sodium | Sodium Methylparaben (and) Sodium Ethylparaben (and) Sodium Butyl paraben (and) Sodium Propylparaben (and) Sodium Isobutylparaben | 0.15 |
| PHASE B | | |
| Parsol MCX | Ethylhexyl Methoxycinnamate | 7.50 |
| Eusolex 4360 | Benzophenone-3 | 3.00 |
| Parsol 1789 | Butyl Methoxydibenzoyl-methane | 2.00 |
| Myritol 318 | Caprylic/Capric Triglyceride | 4.00 |
| Emulgade SEV | Hydrogenated Palm Glycerides (and) Ceteareth-20 (and) Ceteareth-12 (and) Cetearyl Alcohol | 5.00 |
| Propylparaben | Propylparaben | 0.15 |
| Nacol 16-98 | Cetyl Alcohol | 1.00 |
| PHASE C | | |
| TEA | Triethanolamine | 0.20 |
| PHASE D | | |
| Hydrolyzate of Example 1 | | 0.5% |
| Fragrance | Parfum (Fragrance) | qsp |
| Colorant | | qsp |

The constituents of phase A and phase B were heated separately to between 70° C. and 75° C. Phase B was emulsified in phase A, with mixing. Phase C was added at 45° C., increasing the mixing. Phase D was then added when the temperature had dropped below 40° C. Cooling was continued to 25° C. with vigorous mixing.

2—After-Sun Milk:

| Commercial names | INCI names | % by weight |
|---|---|---|
| PHASE A | | |
| Montanov L | C14-22 Alcohols (and) C12-20 Alkyl Glucoside | 3.00 |
| Waglinol 2559 | Cetearyl Isononanoate | 4.00 |
| Tegosoft TN | C12-15 Alkyl Benzoate | 3.00 |
| Abricot kernel oil | Prunus Armeniaca (Apricot) Kernel Oil | 2.00 |
| Avocado oil | Persea Gratissima (Avocado) Oil | 1.00 |
| Abil 350 | Dimethicone | 1.00 |
| PHASE B | | |
| Demineralized water | Aqua (Water) | qsp |
| PHASE C | | |
| Simulgel EG | Sodium Acrylate/Acryloyldimethyl Taurate Copolymer (and) Isohexadecane (and) Polysorbate 80 Copolymer (and) Polysorbate 80 | 0.4 |
| PHASE D | | |
| Phenonip | Phenoxyethanol (and) Methylparaben (and) Ethylparaben (and) Butylparaben (and) Propylparaben (and) Isobutylparaben Ethylparaben and Propylparaben and Butylparaben | 0.30 |
| Germall 115 | Imidazolidinyl Urea | 0.20 |
| PHASE E | | |
| Peptide hydrolyzate of Example 1 | | 0.1% |

Phase A was prepared with mixing. The xanthan gum was incorporated gradually, with deflocculating mixing. Phases C and D were incorporated once gelling was complete. Phase E, which had already been prepared to dissolve the DHA completely, was then added. The pH was adjusted to 4-4.5% if necessary. Colour and fragrance were added.

3—Day Protection Cream:

| Commercial names | INCI names | % by weight |
|---|---|---|
| Phase A | | |
| Emulium Delta | Cetyl alcohol (and) Glyceryl Stearate (and) PEG-75 Stearate (and) Ceteth-20 (and) Steareth-20 | 4.00 |
| Lanette O | Cetearyl Alcohol | 1.50 |
| D C 200 Fluid/100 cs | Dimethicone | 1.00 |
| DUB 810C | Coco Caprylate/Caprate | 1.00 |
| DPPG | Propylene Glycol Dipelargonate | 3.00 |
| DUB DPHCC | Dipentaerythrityl Hexacaprylate/Hexacaprate | 1.50 |
| Cegesoft PS6 | Vegetable Oil | 1.00 |
| Vitamin E | Tocopherol | 0.30 |
| Phenonip | Phenoxyethanol (and) Methylparaben (and) Ethylparaben (and) Butylparaben (and) Propylparaben (and) Isobutylparaben | 0.70 |
| Phase B | | |
| Demineralized water | Aqua | qsp 100 |
| Glycerin | Glycerin | 2.00 |
| Carbopol EDT 2020 | Acrylates/C10-30Alkyl Acrylate Crosspolymer | 0.15 |
| Keltrol BT | Xanthan Gum | 0.30 |
| Phase C | | |
| Sodium Hydroxide (10% solution) | Sodium Hydroxide | 0.30 |
| Phase D | | |
| Demineralized water | Aqua | 5.00 |
| Stay-C 50 | Sodium Ascorbyl Phosphate | 0.50 |
| Phase E | | |
| Butylene Glycol | Butylene Glycol | 2.00 |
| Dekaben CP | Chlorphenesin | 0.20 |
| Phase F | | |
| GP4G Hydrolyzate of Example 1 | Water (and) *Artemia* Extract | 1.00 2% |

Phase A was prepared and heated to 75° C., with mixing. Phase B was prepared by dispersing the carbopol then the xanthan gum, with mixing. It was allowed to stand, then heated to 75° C.

Once at temperature, A and B were emulsified in a rotor-stator mixer. It was neutralized with phase C, with rapid mixing. After cooling to 40° C., phase D was added followed by phase E. Cooling was continued with gentle mixing and phase F was added.

Applicants incorporate by reference the material contained in the accompanying computer readable Sequence Listing entitled "US09-124SequenceListing.txt", which was created on Jan. 3, 2012, and is 2,242 bytes in size, and hereby confirm that the information recorded in the computer readable form is identical to the written sequence listing.

The invention claimed is:

1. A method for soothing sensitive skin, the method comprising:
   providing a composition comprising a peptidic hydrolyzate comprising a bioactive peptide comprising 4 to 6 amino acids comprising at least one glycine residue, one leucine residue, and one glutamic acid residue; as an active principle agent activating 3-hydroxy-3-methyl-glutaryl-Coenzyme A (HMG-CoA) reductase; and
   topically applying the composition to the skin to be treated.

2. The method of claim 1, wherein the composition further comprises a suitable medium selected from the group consisting of water, glycerol, ethanol, propylene glycol, butylene glycol, dipropylene glycol, ethoxylated or propoxylated diglycols, cyclic polyols, vaseline, a vegetable oil, and combinations thereof; and the peptidic hydrolyzate reinforces the barrier function of the epidermis.

3. The method of claim 1, wherein said bioactive peptide has general formula (I):

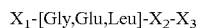

in which,
X₁ is alanine, valine, isoleucine or absent,
X₂ is serine or threonine,
X₃ is leucine, isoleucine or absent.

4. The method of claim 3, wherein said bioactive peptide is selected from the group consisting of:

```
                                    (SEQ ID NO: 1)
Ala-Gly-Glu-Leu-Ser-Ile, (SEQ ID NO: 2)
Leu-Gly-Glu-Ser-Leu, (SEQ ID NO: 3)
Val-Gly-Glu-Leu-Thr, (SEQ ID NO: 4)
Ile-Gly-Glu-Leu-Ser, (SEQ ID NO: 5)
Ala-Gly-Glu-Leu-Ser, (SEQ ID NO: 6)
Gly-Glu-Leu-Thr-Ile, and (SEQ ID NO: 7)
Gly-Glu-Leu-Ser.
```

5. The method of claim 1, wherein said peptidic hydrolyzate originates from the hydrolysis of plants selected from the group consisting of einkorn (*Triticum monococum*), potato (*Solanum tuberosum*), corn (*Zea mayz* L.), barley (*Hordeum vulgare* L.), and rapeseed (*Brassica napus*).

6. The method of claim 1, wherein said peptidic hydrolyzate contains said bioactive peptide in the range of 0.5 to 5.5 g/l.

7. The method of claim 1, wherein said peptidic hydrolyzate is present in a quantity representing 0.0001% to 20% of the total composition weight.

8. The method of claim 1, wherein the peptidic hydrolyzate is present in a quantity representing from 0.05% to 5% of the total weight of the composition.

9. The method according to claim 1, further comprising dissolving said peptidic hydrolyzate in one or more solvents selected from the group consisting of water, glycerol, ethanol, propylene glycol, butylene glycol, dipropylene glycol, ethoxylated or propoxylated diglycols, cyclic polyols, vaseline, a vegetable oil, and combinations thereof.

10. The method of claim 1, wherein the composition is present in a form suitable for topical application.

11. The method of claim 1, wherein the composition further comprises at least one first active principle agent promoting the action of said peptidic hydrolyzate selected from the group consisting of other peptide active agents, plant extracts, healing agents, anti-ageing agents, anti-wrinkle agents, soothing agents, free radical scavengers, antioxidizing agent, ultraviolet (UV) screens, agents stimulating the synthesis of dermal macromolecules or energy metabolism, moisturizers, antibacterial agents, antifungal agents, anti-inflammatory agents, anaesthetics, agents modulating skin differentiation or pigmentation or skin depigmentation, and agents stimulating the growth of the nails or hair.

12. The method of claim 1, wherein the composition further comprises at least one second active principle selected from the group consisting of glycolic acid, lactic acid, malic acid, citric acid, tartaric acid, mandelic acid, salicylic acid, ascorbic acid or vitamin C, retinol, retinal, retinoic acid, minoxidil, lithium salts, para-phenylene diamine (p-PDA), N-phenyl p-PDA and toluene 2,5-diamine sulphate, meta-phenylene diamine (m-PDA), toluene, 3,4-diamine, ortho-phenylene diamine (o-PDA), fragrancing alcoholic solutions, aluminum salts, thiols, ammonia, and hydroquinone, the second active principle providing a secondary irritant effect.

13. The method of claim 1, the method comprising:
providing a composition comprising a bioactive peptide selected from the group consisting of:

```
                                    (SEQ ID NO: 1)
Ala-Glu-Gly-Leu-Ser-Ile, (SEQ ID NO: 2)
Leu-Gly-Glu-Ser-Leu, (SEQ ID NO: 3)
Val-Gly-Glu-Leu-Thr, (SEQ ID NO: 4)
Ile-Gly-Glu-Leu-Ser, (SEQ ID NO: 5)
Ala-Gly-Glu-Leu-Ser, (SEQ ID NO: 6)
Gly-Glu-Leu-Thr-Ile, and (SEQ ID NO: 7)
Gly-Glu-Leu-Ser,
``` wherein the composition treats skin irritations.

14. The method of claim 1, the method comprising:
providing a composition comprising a bioactive peptide selected from the group consisting of:

```
                                    (SEQ ID NO: 1)
Ala-Glu-Gly-Leu-Ser-Ile, (SEQ ID NO: 2)
Leu-Gly-Glu-Ser-Leu, (SEQ ID NO: 3)
Val-Gly-Glu-Leu-Thr, (SEQ ID NO: 4)
Ile-Gly-Glu-Leu-Ser, (SEQ ID NO: 5)
Ala-Gly-Glu-Leu-Ser, (SEQ ID NO: 6)
Gly-Glu-Leu-Thr-Ile, and (SEQ ID NO: 7)
Gly-Glu-Leu-Ser,
``` wherein the composition limits the effects of external stresses chosen from ultraviolet (UV) radiation or oxidizing agents on skin.

15. The method of claim 1, the method comprising:
providing a composition comprising a bioactive peptide selected from the group consisting of:

```
                                    (SEQ ID NO: 1)
Ala-Glu-Gly-Leu-Ser-Ile, (SEQ ID NO: 2)
Leu-Gly-Glu-Ser-Leu,
```

-continued

Val-Gly-Glu-Leu-Thr, (SEQ ID NO: 3)

Ile-Gly-Glu-Leu-Ser, (SEQ ID NO: 4)

Ala-Gly-Glu-Leu-Ser, (SEQ ID NO: 5)

Gly-Glu-Leu-Thr-Ile, (SEQ ID NO: 6)
and

Gly-Glu-Leu-Ser, (SEQ ID NO: 7)

wherein the composition is a pharmaceutical composition that treats skin inflammation, or pruritus, hives, insect bites, allergies or alopecia in its inflammatory phases.

\* \* \* \* \*